(12) United States Patent
Weber et al.

(10) Patent No.: US 8,404,165 B2
(45) Date of Patent: Mar. 26, 2013

(54) CATHETER DISTAL TIP DESIGN AND METHOD OF MAKING

(75) Inventors: Jan Weber, Maple Grove, MN (US); Thomas J. Holman, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1205 days.

(21) Appl. No.: 11/262,690

(22) Filed: Oct. 31, 2005

(65) Prior Publication Data

US 2006/0052767 A1     Mar. 9, 2006

Related U.S. Application Data

(62) Division of application No. 10/824,996, filed on Apr. 14, 2004, now abandoned.

(51) Int. Cl.
  *B29C 37/02*     (2006.01)
(52) U.S. Cl. ........................................ 264/138
(58) Field of Classification Search .................. 264/400, 264/139, 156, 138; 604/523
See application file for complete search history.

(56) References Cited

U.S. PATENT DOCUMENTS

| | | | |
|---|---|---|---|
| 3,862,635 A | 1/1975 | Harautuneian | 128/207.15 |
| 3,884,242 A | 5/1975 | Bazell et al. | 128/207.15 |
| 4,385,635 A | 5/1983 | Ruiz | 128/658 |
| 4,801,297 A | 1/1989 | Mueller | 604/523 |
| 4,921,483 A | 5/1990 | Wijay et al. | 604/96 |
| 5,250,059 A | 10/1993 | Andreas et al. | 606/159 |
| 5,300,032 A | 4/1994 | Hibbs et al. | 604/64.1 |
| 5,425,712 A | 6/1995 | Goodin | 604/96 |
| 5,769,830 A | 6/1998 | Parker | 604/282 |
| 5,993,415 A | 11/1999 | O'Neil et al. | 604/96 |
| 6,113,579 A | 9/2000 | Eidenschink et al. | 604/264 |
| 6,156,054 A | 12/2000 | Zadno-Azizi et al. | 606/194 |
| 6,165,152 A | 12/2000 | Becker et al. | 604/96.01 |
| 6,245,053 B1 | 6/2001 | Benjamin | 604/523 |
| 6,325,790 B1 | 12/2001 | Trotta | 604/523 |
| 6,355,027 B1 | 3/2002 | Le et al. | 604/525 |
| 6,368,301 B1 | 4/2002 | Hamilton et al. | 604/103 |
| 6,403,011 B1 | 6/2002 | Stamberg | 264/400 |
| 6,503,353 B1 * | 1/2003 | Peterson et al. | 156/86 |
| 6,514,228 B1 * | 2/2003 | Hamilton et al. | 604/96.01 |
| 6,517,515 B1 | 2/2003 | Eidenschink | 604/101.05 |
| 6,537,480 B1 * | 3/2003 | Becker et al. | 264/400 |
| 6,622,367 B1 | 9/2003 | Bolduc et al. | 29/447 |
| 6,692,461 B2 | 2/2004 | Wantink | 604/103 |

(Continued)

FOREIGN PATENT DOCUMENTS

| | | |
|---|---|---|
| EP | 0852955 | 7/1998 |
| EP | 1232765 | 8/2002 |
| GB | 2002677 | 2/1979 |
| WO | 03/013638 | 2/2003 |

OTHER PUBLICATIONS

Afanasiev, Y.V., et al, *Hydrodynamic regimes of UV laser ablation of polmyers*, Applied Physics, vol. A64, No. 6 p. 561-72 (Jun. 1997).

(Continued)

*Primary Examiner* — Larry Thrower
(74) *Attorney, Agent, or Firm* — Vidas, Arrett & Steinkraus, P.A.

(57) ABSTRACT

A catheter comprises a catheter shaft having a distal tip, the distal tip having an inner surface and an outer surface, the inner surface having a rounded profile. The catheter may be made by rounding the inner surface of the distal tip.

10 Claims, 5 Drawing Sheets

U.S. PATENT DOCUMENTS

| | | | |
|---|---|---|---|
| 6,746,424 B2 | 6/2004 | Stamberg | 604/103.06 |
| 2001/0044595 A1 | 11/2001 | Reydel et al. | 604/98.02 |
| 2002/0002363 A1 | 1/2002 | Urakawa et al. | 604/544 |
| 2002/0049424 A1 | 4/2002 | Fulford | 604/529 |
| 2002/0052641 A1 | 5/2002 | Monroe et al. | 623/1.11 |
| 2002/0169457 A1 | 11/2002 | Quinn | 606/108 |

OTHER PUBLICATIONS

Minamitini, Y. & Sasagawa, T., *Excimer laser processing system using holographic optical elements*, Mitsubishi Electric Advance, vol. 81 p. 27-8 (Dec. 1997).

Meijer, J., at al, *Laser machining by short and ultrashort pulses, state of the art and new opportunities in the age of the photons*, CIRP Annals—Manufacturing Technology, v 51 n p. 531-550 (2002).

Golub, Michael & Grossinger, Israel, *Diffractive optical elements for biomedical applications*, Proceedings of SPIE—The International Society for Optical Engineering, v 3199 p. 220-23 (1997).

Andrew, J.E., et al, *Direct etching of polymeric materials using a XeCl laser*, Applied Physics Letters vol. 43, No. 8 p. 717-19 (Oct. 15, 1983).

U.S. Appl. No. 10/824,996, filed Apr. 14, 2004, Weber et al.

* cited by examiner

CATHETER DISTAL TIP DESIGN AND METHOD OF MAKING

This application is a divisional of copending U.S patent application Ser. No. 10/824,996, the entire content of which is incorporated by reference herein.

BACKGROUND OF THE INVENTION

This invention relates to both intravascular and non-vascular catheter assemblies. Catheters are commonly employed in percutaneous intravascular procedures, such as percutaneous transluminal coronary angioplasty (PTCA), for example, to open blocked vessels with as little trauma as possible.

Catheters employed for non-vascular procedures include the catheters employed in the urinary tract, or those employed to examine the lower gastrointestinal tract, for example.

Several different types of catheters are utilized for intravascular treatment including guide catheters, angioplasty catheters, dilatation balloon catheters, medical delivery devices such as stent delivery catheters including both the self-expanding and balloon expandable varieties, angiographic catheters, neural catheters, urinary catheters, gastrointestinal catheters, catheters for the reproductive system, heat transfer catheters, therapeutic delivery devices, thrombectomy devices, intravenous ultrasound systems, electrophysiology devices, endoscopic devices, and so on and so forth.

In intravascular procedures, guide catheters are commonly used to aid in delivering a balloon catheter or other interventional medical devices to a treatment site in a vessel or other lumen within the body.

In a routine coronary angioplasty procedure, a guide catheter is introduced through the aorta until the distal end of the guide catheter is engaged with the coronary ostium. Guide catheters typically have a preformed distal tip. The distal portion of the guiding catheter is located within the ascending aorta with the distal tip of the guiding catheter seated in the ostium. The proximal end of the guiding catheter is torqued from outside the patient to guide the distal tip of the guiding catheter into the ostium. Guide catheters typically have preformed bends formed along their distal portion to facilitate placement of the distal end of the guide catheter into the ostium of a patient. Guide catheters preferably have a relatively stiff main body portion and softer distal tip. The stiff main body portion provides the guide catheter with sufficient "pushability" and "torqueability" to allow the guide catheter to be inserted percutaneously through a peripheral artery, moved and rotated to position the distal end of the catheter at the desired aligning angle relative to the ostium. In addition, a soft distal tip at the very distal end of the catheter should be used to minimize the risk of causing trauma to a blood vessel wall while the guide catheter is being moved through the vasculature to the ostium.

Next, the guidewire is advanced past the distal end of the guide catheter within the lumen of the diseased vessel and manipulated across the region of the stenosis. The balloon dilatation catheter is then advanced past the distal end of the guide catheter over the guidewire until the balloon is positioned across the treatment site. After the balloon is inflated to dilate the blood vessel in the region of the treatment site, the guidewire, balloon dilatation catheter and guide catheter can be withdrawn.

Typical commercially available intravascular balloon catheters used for angioplasty and other vascular procedures usually have an elongated shaft with an inflatable dilatation member on a distal portion of the shaft and a fitting on the proximal end of the shaft for the delivery of inflation fluid through an inner lumen extending through the catheter shaft to the interior of the inflatable dilatation member.

Once in position, the balloon is inflated by supplying fluid under pressure through an inflation lumen in the catheter to the balloon. The inflation of the balloon causes stretching of the artery and pressing of the lesion into the artery wall, to reestablish acceptable blood flow through the artery There are two common types of balloon catheters commonly referred to as "over-the-wire" (OTW) catheters and fixed wire catheters. An over-the-wire catheter is one in which a separate guide wire lumen is provided in the catheter so that a guide wire can be used to establish the path through the stenoses. The dilatation catheter can then be advanced over the guide wire until the balloon on the catheter is positioned within the stenoses. There is also a modification of an OTW catheter which is referred to as a single-operator-exchange (SOE) or rapid exchange (RE) catheter. SOE catheters have a guide wire lumen that only extends through a portion of the catheter. The guide wire lumen extends from the distal end of the catheter to a distal porthole on the catheter tube.

A fixed wire catheter acts as its own guide wire, and thus there is no need for a separate guide wire lumen.

Angiographic catheters can be used in evaluating the progress of coronary artery disease in patients. Angiography procedures are used to view the patency of selected blood vessels. In carrying out this procedure, a diagnostic catheter also having a desired distal end curvature configuration may be advanced through the vascular system of the patient until the distal end of the catheter is steered into the ostium.

The profile of the outer surface of the distal tip of a catheter may be rounded so as to result in a tip which reduces the likelihood of trauma to the vessel. However, rounding the tip on the outside using current methods, may leave the edge of the tip on the inner lumen sharp. When the catheter is advanced over the guidewire, or when the guidewire is retracted into the catheter, this sharp edge can act similar to a knife, scraping material from the guidewire, and can increase the friction between the inner catheter shaft and the guidewire. If a lubricious coating is present, this may also be scraped off. Furthermore, having a sharp tip on the inner lumen can results in parts of the tip which actually break off from the catheter.

There remains a need in the art for a catheter having an inner distal tip which has a smoother, more rounded profile.

SUMMARY OF THE INVENTION

The present invention, in one embodiment, relates to a catheter assembly having a distal tip having an inner and an outer surface, wherein at least the inner surface has a longitudinal cross-sectional profile view of the distal tip wherein the inner surface curves toward the outer surface at the distal end, and desirably both the inner and the outer surface have a curved profile.

In one embodiment, the curve has a radial arc.

The rounded or curved profile may be formed using any technique known in the art. In some embodiments, laser energy is employed. As used herein, the term "rounded" or "rounding" shall hereinafter refer to curvature in a region or to providing curvature to a region.

Lasers suitable for use herein are those which generate energy having a wavelength of about 450 nm or less, suitably about 350 nm or less, more suitably 250 nm or less and even more suitably about 200 nm or less. Excimer lasers are suitable for use herein and are capable of generating energy in the UV range at wavelengths of about 450 nm or less. For example, the argon-fluoride (ArF) excimer laser produces UV radiation having a wavelength of 193 nm and the fluorine (F2) laser produces UV radiation having a wavelength of 157 nm. An example of one type of laser which is suitable for use herein is an excimer laser. One example of an excimer laser which produces UV radiation having a wavelength of over 200 nm is krypton-fluoride (KrF) excimer laser which produces UV radiation having a wavelength of 248 nm.

Excimer lasers are advantageous because they produce a very highly uniform beam, i.e. uniformity of intensity across the beam diameter.

The present invention also relates to a method of producing a catheter having a distal tip having an inner surface and an outer surface, wherein the inner surface is formed by applying a laser beam to at least the inner surface of the distal tip. The resultant distal tip has an inner surface having a rounded profile. Desirably, the laser beam is applied to the outer surface as well, resulting in the outer surface of the distal tip having a rounded profile as well.

Providing a catheter having a distal tip with a curved profile reduces the likelihood of scraping by the inner surface of the distal tip on a guide wire being advanced therethrough, and reduces the likelihood of trauma to the vessel produced by the tip because rounding the inner surface reduces the sharpness of the inner edge as well.

DETAILED DESCRIPTIONS OF THE INVENTION

While this invention may be embodied in many different forms, there are described in detail herein by way of illustration, specific embodiments of the invention. This description is an exemplification of the principles of the invention and is not intended to limit the invention to the particular embodiments illustrated.

Any U.S. patents and applications, and all other published documents mentioned anywhere in this application are incorporated herein by reference in their entirety.

In one embodiment, the present invention relates to a catheter having a distal tip, the distal tip having an inner surface and an outer surface, and in a longitudinal cross-sectional profile view of the distal tip, the inner surface curves towards the outer surface at the distal end. In one embodiment, the curve has a radial arc.

The outer surface may also have a curved profile wherein it curves inward toward the inner surface at the distal tip, or the outer surface may have a profile which remains substantially the same from the proximal end of the distal tip to the distal end of the distal tip.

Rounding or curving of the inner and/or the outer surface, can result in a tip which is less traumatic to a vessel during use. The rounded profile of the inner surface of the distal tip can decrease the amount of friction during contact with a second surface such as a guide wire, for example.

In the case of an angioplasty balloon catheter, rounding of the inner surface can result in a smoother surface, reducing the likelihood of scraping material from the guide wire, or scraping catheter lubricant from both.

Further, the use of softer polymeric materials in combination with a curved inner surface profile may further reduce the likelihood of breakage or tearing of the catheter tip which can occur with a sharp, non-rounded inner profile.

Figure 1:
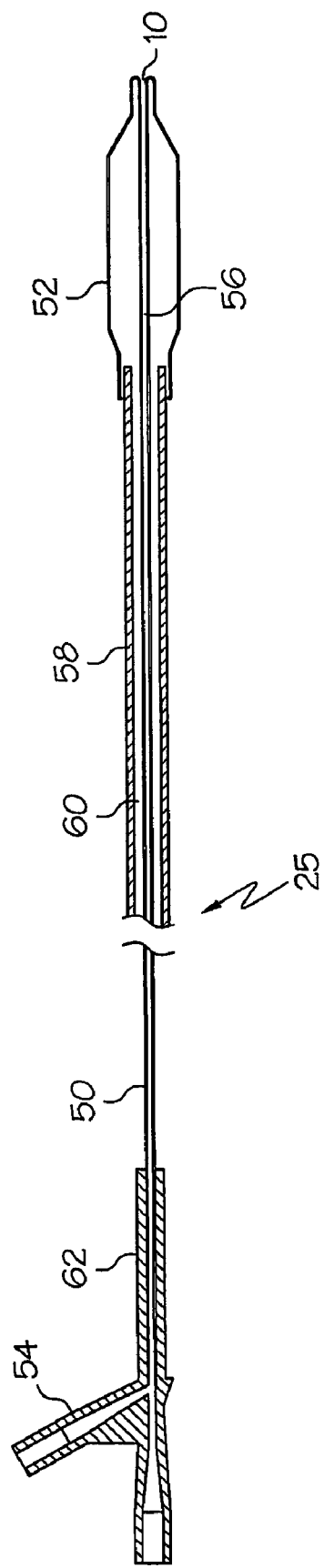
FIG. 1 is a perspective side view of a balloon catheter assembly in accordance with the invention.

Turning now to the figures, represented generally at 25 in FIG. 1, is a representative OTW angioplasty balloon catheter according to the invention. Such balloon catheters are discussed, for example, in commonly assigned U.S. Pat. Nos. 6,113,579, 6,517,515, 6,514,228, each of which is incorporated by reference herein in its entirety. In this embodiment, catheter 25 has an elongate shaft assembly 50 and a balloon assembly 52. A conventional OTW-type manifold assembly 54 is connected to proximal end of shaft assembly 50. The shaft assembly 50 includes an inner tube 56 and an outer tube 58. Outer tube 58 is coaxially disposed about inner tube 56 to define an annular inflation lumen 60. In this embodiment, distal tip 10 of inner tube 56 has a curved inner profile which when viewed in a longitudinal cross-sectional view, shows a curvature from the inner surface to the outer surface at the distal end 18 of the distal tip 10, according to the invention. Manifold assembly 54, is further shown with a strain relief 62.

Figure 2:
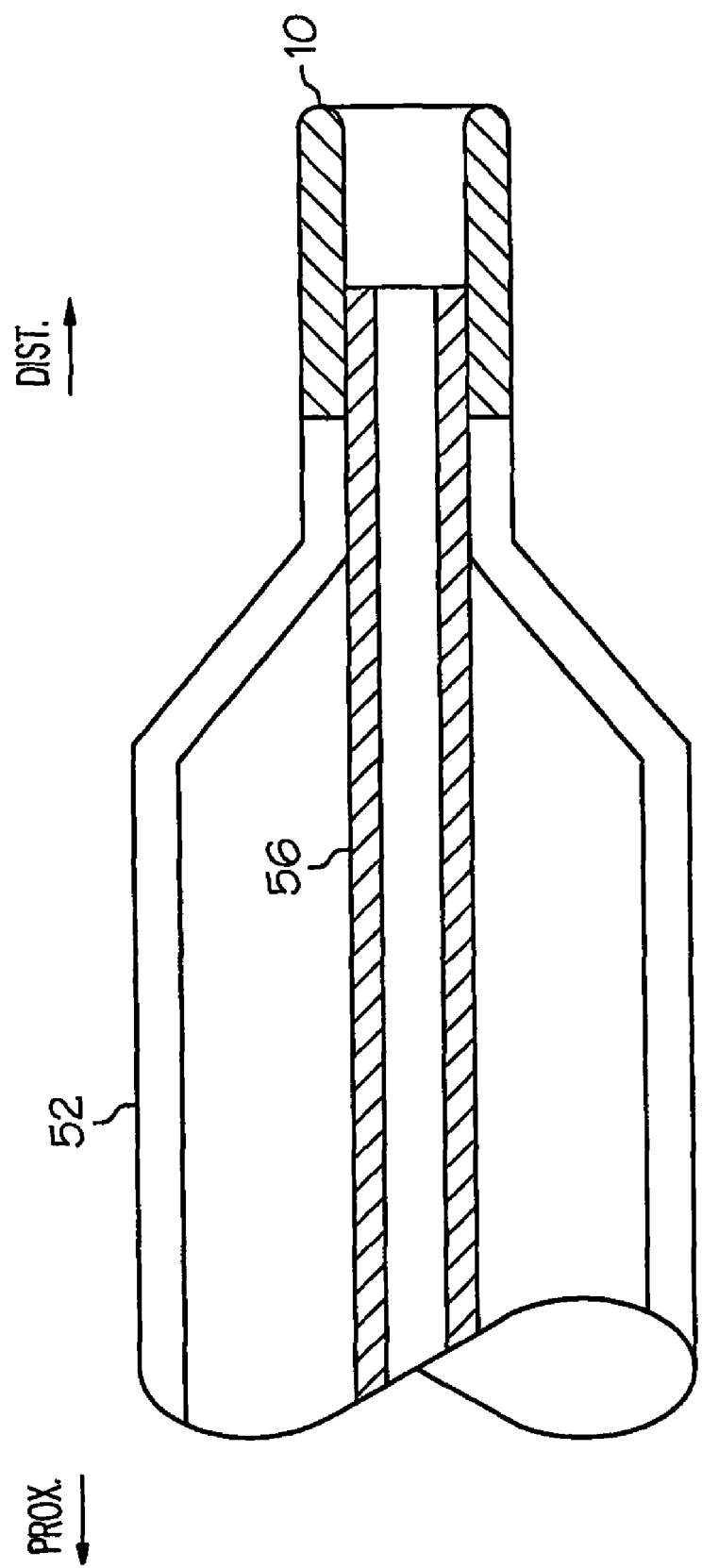
FIG. 2 is cross-sectional view of the distal end of balloon catheter assembly as shown in FIG. 1.

FIG. 2 is a cross-sectional view of the distal end of the catheter assembly showing balloon 52 over inner tube 56 having distal tip 10 according to the invention. Distal tip 10 of balloon 52 may be formed having a smooth, rounded inner profile (not shown). Distal tip 10 may be formed from the same material or from a different material than that of balloon 52. Distal tip 10 may comprise a soft material that minimizes trauma to the surrounding tissue as catheter 25 is advanced to its final destination within the vasculature. Additionally, the rounding of the tip on the outer surface as well as on the inner surface, further reduces the likelihood of trauma to surrounding tissue.

This description of a balloon catheter is intended for illustrative purposes only, and not as a limitation on the scope of the present invention. There are variations in the design of such devices known to those of skill in the art.

Figure 3:
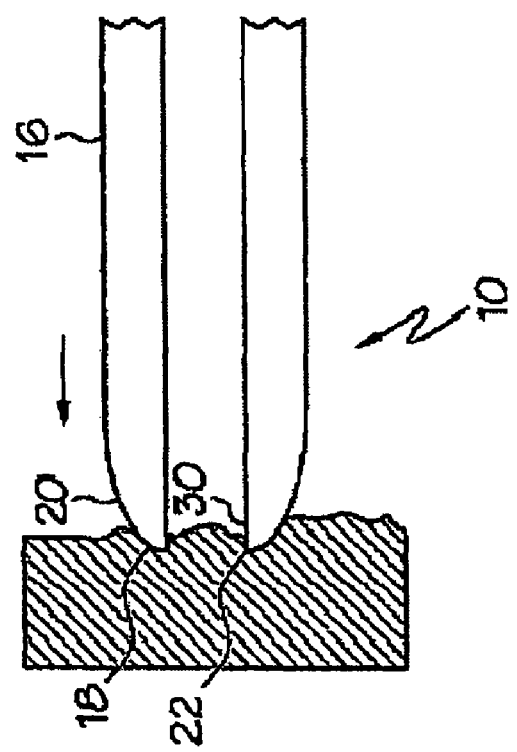
FIG. 3 is a diagrammatic longitudinal cross-sectional partial view of a traditional distal tip for a catheter shaft.

The distal tip design according to the invention offers a rounded, softer tip design which may result in less trauma to the vessels through which the catheter assembly is delivered. FIG. 3, in contrast, is a representative diagrammatic longitudinal cross sectional partial view of a traditional distal tip 10 for a catheter assembly. Distal tip 10 has a proximal end 16 and a distal end 18 and a curved outer surface 20 but a sharp inner surface 30 at the distal tip in the region where the tip opening is located.

Figure 4:
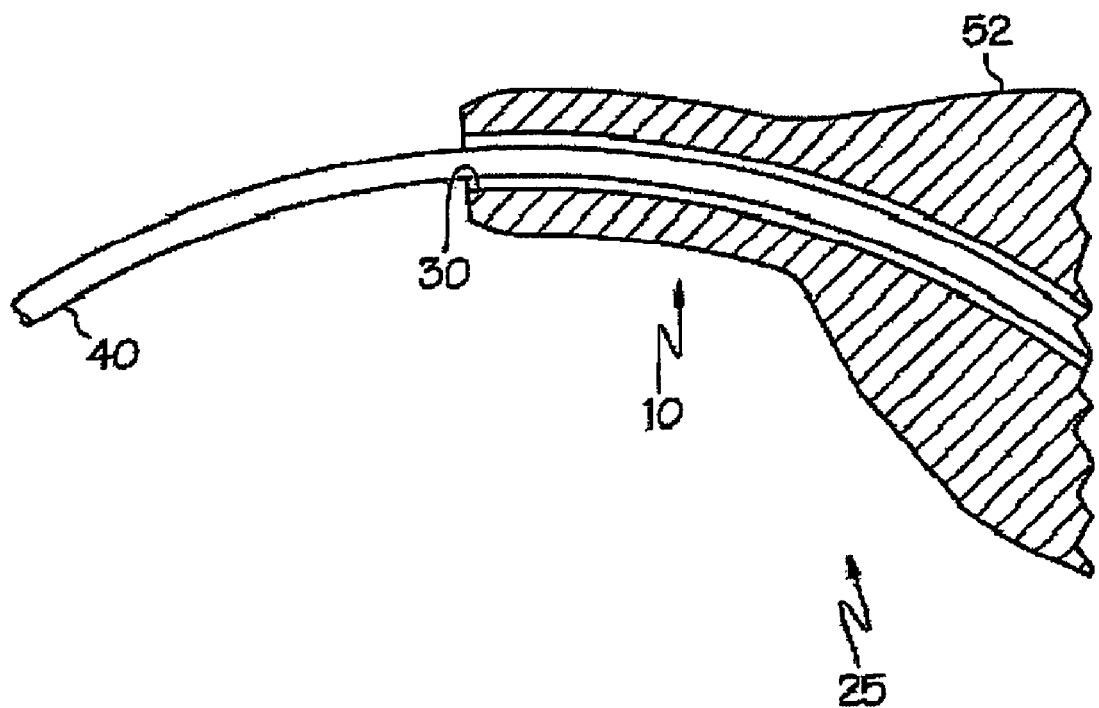
FIG. 4 is a partial side view of a traditional distal tip of a balloon catheter assembly according to the invention.

FIG. 4 is a partial side view of a simple OTW balloon catheter 25 being advanced from the proximal end (not shown) over a guide wire 40. As can be seen from FIG. 3, the inner surface 30 of the distal tip 10 of balloon catheter 25 is sharp in the traditional sense. If the guide wire 40 is provided with a lubricious coating, for example, this sharp edge 30 may cause scraping of the lubricious coating from the surface of the guide wire 40.

Figure 5:
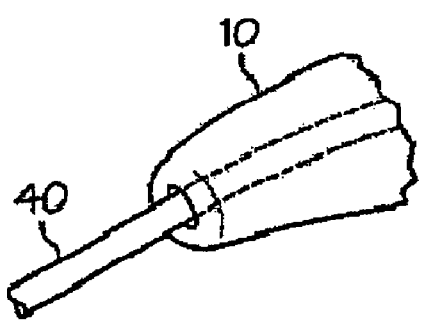
FIG. 5 is a partial perspective view of a distal tip of a balloon catheter assembly according to the invention.

FIG. 5 is a perspective partial view of the distal tip 10 of an OTW catheter shown in combination with a guide wire 40. In this embodiment, the inner profile has been rounded, reducing the sharp inner edge 30 as shown in FIGS. 1 and 2.

Figure 6:
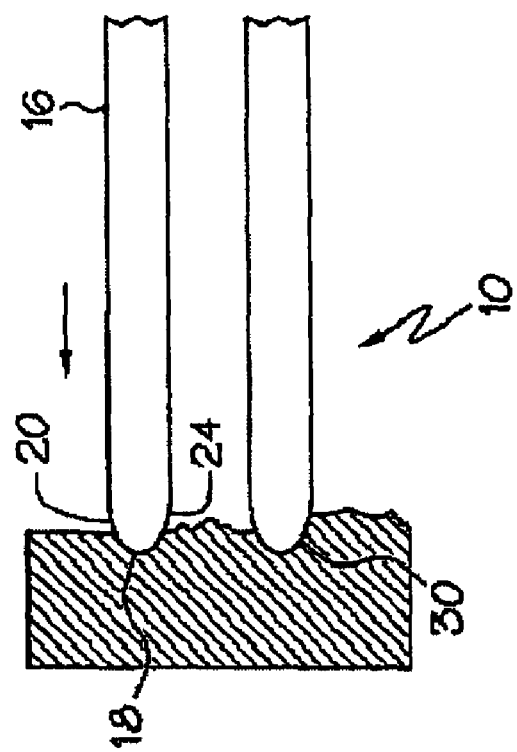
FIG. 6 is a diagrammatic longitudinal cross-sectional partial view of a distal tip for a catheter assembly according to the invention.

FIG. 6 is a diagrammatic representation of a longitudinal cross section of the distal tip 10 shown as a partial view. In this embodiment, distal tip 10 has a proximal end 16 and a distal end 18 and is shown having both a curved outer profile 30 and in a longitudinal cross-sectional profile view of the distal tip, an inner surface 20 which curves toward the outer surface at the distal tip, reducing the sharpness of edge 22 shown in FIGS. 1 and 2 which may also reduce the likelihood of trauma to a patient's vessel, as well as reducing the likelihood of scraping of the guide wire surface. Furthermore, scraping, as discussed above, may have a negative impact on a lubricious coating such as on a guide wire, or on the catheter surface itself. As can be seen in FIG. 4, the circumference of the inner surface increases slightly from the proximal end 16 to the distal end 18 of the inner surface. The circumference of the outer surface may decrease slightly from the proximal end 16 to the distal end 18 of the distal tip, or the circumference of the outer surface may remain substantially unchanged as well.

The smoother, rounded inner edge, also reduces the likelihood of a scraping effect on any adjacent surface with which the distal tip may come in slidable contact. In this embodiment, the curvature of the outer surface is shown substantially equal to and opposite the curvature of the inner surface, or in other words, the curvature of the outer surface is substantially a mirror image of the inner surface.

The shape of the catheter inner and/or outer surface, shall not be intended to be limited to those which are purely circular. Other geometries are contemplated herein. For example, the shape could be elliptical as well.

Distal tip 10 may be formed from the same material, or from a different material than the catheter shaft. Any suitable polymeric material may be employed herein and include both elastomers and non-elastomeric polymers.

Suitable materials may include, but are not limited to, polyolefins including polyethylene, polyamides including nylon and copolymers such as poly(ether-block amide), polyimides, polyurethanes, polyesters including the PET (polyethylene terephthalate) and PBT (polybutylene terephthalate) copolymers and elastomeric polyesters such as poly(ether-block-ester), latex, silicones, rubbery block copolymers such as styrenic block copolymers including SEBS (styrene-ethylene/butylenes-styrene), SIS (styrene-isoprene-styrene), SBS (styrene-butadiene-styrene), SEPS (Styrene-ethylene/propylene-styrene), butylene and isobutylene rubber, and so forth, any copolymers thereof, and mixtures thereof. As used herein, the term "copolymer" shall be used to refer to any polymer formed from two, three or more monomers. Some of the above classes of materials such as the polyesters, for example, include both elastomeric and non-elastomeric polymers in the class. The above list is not exhaustive, and is not intended to limit the scope of the present invention. Many suitable polymeric materials not listed here, are known to those of skill in the art.

In some embodiments, the material of the distal tip may be formed from a material which is softer than that of the shaft. Typically, these properties are measured using a Shore Durometer scale. The Shore Durometer hardness of the distal tip in these embodiments may be less than the Shore Durometer of the catheter shaft, or of at least a portion of the shaft.

Other embodiments, as in the case of a chronic total occlusion (CTO) device, the distal tip may be formed from a material which is not softer than that of the catheter shaft.

In one embodiment, the rounded inner edge may be formed using laser ablation techniques. However, any known techniques, such as abrasion for example, of rounding the inner edge and/or outer edge may be employed.

Lasers may be employed in rounding the inner and/or outer edge of the distal tip. Suitable lasers which may be employed include those producing energy at a wavelength of about 450 nm or less.

One example of a laser employed is an excimer laser. Excimer lasers are pulsed gas discharge lasers which produce wavelength output in the ultraviolet region of the spectrum. The wavelength output depends upon the active gas fill of the laser. For example, the argon-fluoride (ArF) excimer laser produces UV radiation having a wavelength of 193 nm and the fluorine (F2) laser produces UV radiation having a wavelength of 157 nm. One example of an excimer laser which produces UV radiation having a wavelength of over 200 nm is krypton-fluoride (KrF) excimer laser which produces UV radiation having a wavelength of 248 nm. Xenon-chloride excimer lasers produce UV radiation having a wavelength of 308 nm and xenon-fluoride excimer lasers produce UV radiation having a wavelength of 351 nm.

In one embodiment, the laser employed is the ArF excimer laser generating UV radiation at a wavelength of 193 nm.

In another embodiment, the laser employed is the F2 excimer laser which generates UV radiation at a wavelength of 157 nm.

Excimer lasers are advantageous because they produce a very short pulse length which allows the materials to be ablated rather than melted. A typical Excimer laser has a pulse length of the order of nanoseconds. Femtosecond lasers may also be advantageously employed in the present invention.

Excimer lasers also produce a very highly uniform beam, i.e. uniformity of intensity across the beam diameter.

The lower the wavelength employed, the higher the absorption by the polymer which makes ablating at the lower wavelengths of about 250 nm or less, much more precise than the higher wavelengths.

The process of laser ablation involves directing a laser at a desired location of the distal tip and ablating the material in the desired pattern on the inner and/or outer surface of the distal tip.

The process of laser ablation has a threshold fluence. Fluence is a level of required energy density, and is a measurement of the projected laser pulse energy per unit area per pulse on the substrate, which may be varied by either changing the laser pulse energy, or by changing the ablation area. At fluences below a certain threshold, $F_{th}$, only minuscule etching (<0.05 µm per laser pulse) is observed. Thus, it is necessary to maintain the laser fluence above the threshold. When laser fluence is above the threshold, the etch depth, d, per pulse increases rapidly with increasing fluence. At a fluence just above the threshold, the etch depth, d, per pulse varies logarithmically with the fluence, F:

$$d \approx \ln(F/F_{th})$$

With the increase of fluence, the relationship between etch depth and fluence changes from logarithmic to approximately linear. UV laser ablation of polymers is described in, for example in an article by Y. V. Afanasiev et al., *Hydrodynamic regimes of UV laser ablation of polymers*, Applied Physics, A64, 561-572 (1997) which is incorporated by reference herein in its entirety.

One way in which to create the rounded tip both on the inner and the outer surface of the distal tip, is to direct the laser beam along the axial direction and provide a fluence profile as shown in FIG. 5.

Figure 7:
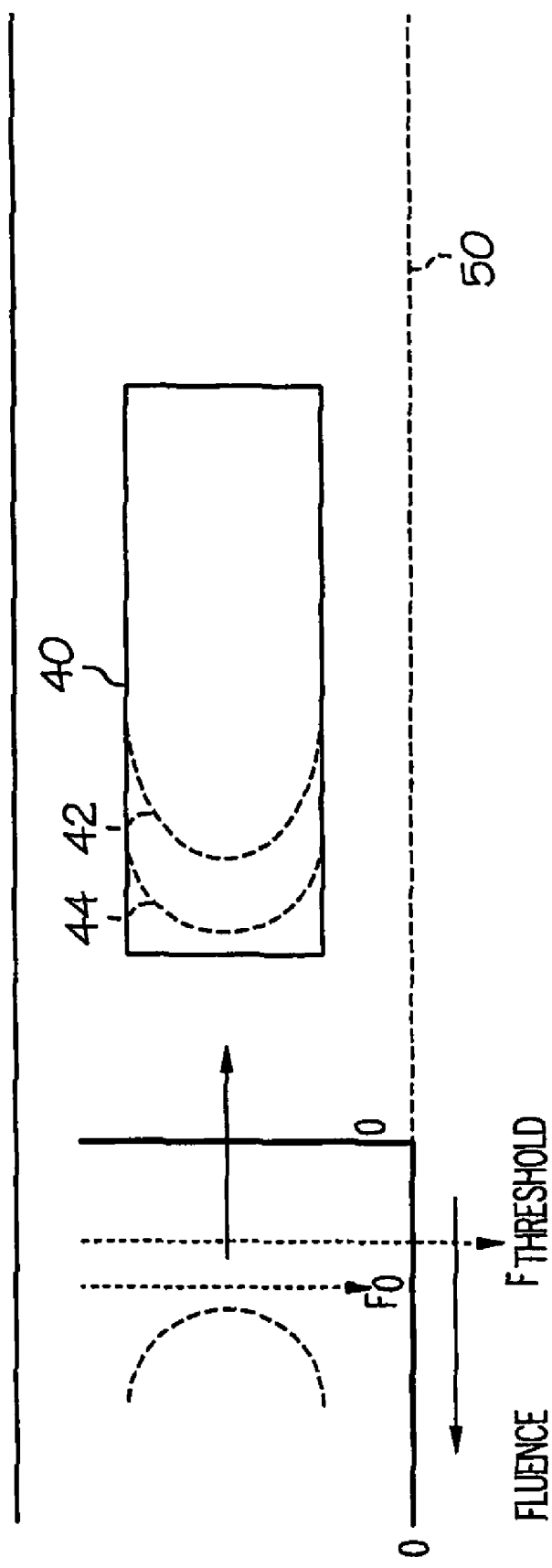
FIG. 7 is a fluence profile which may be employed for forming a distal tip by laser ablation according to the invention.

In FIG. 7, half of the tubular member is represented as can be seen from the location of the inner lumen axis 50. In the case of a round tube, the required fluence profile may be obtained by forming an annular beam profile with an energy profile which is parabolic in a radial direction with a minimum density level just above the threshold fluence in between the inner and outer radius of the annulus. The annular shape is projected by means of lenses on the tip of the catheter such that the outer circumference of the annular shape is projected on the outer circumference of the tube and the inner circumference of the annulus on the inner circumference of the tube. FIG. 3 illustrates, in part, that the extent of the rounding and the resulting profile of the tip will be a function of the number of pulses. Thus, after 50 pulses, shown at curve 42, the curvature will be greater than after 10 pulses, shown at curve 44.

The method according to the invention may be employed in the formation of a distal tip for a catheter shaft employed in any type of catheter assembly used in intravascular procedures as well as non-vascular procedures including, but not limited to, guide catheters, balloon angioplasty catheters, i.e. dilatation catheters, SOE or RE catheters, OTW catheters, fixed wire catheters, medical device delivery catheters including the stent delivery devices in both the self-expanding and balloon expandable varieties, therapeutic substance delivery devices, thrombectomy devices, endoscopic devices, angiographic catheters, neuro catheters, dilitation catheters, urinary tract catheters, gastrointestinal catheter devices, heat transfer catheters including thermal catheters and cooling, intravascular ultrasound systems, electrophysiology devices, and so on and so forth.

The above disclosure is intended to be illustrative and not exhaustive. This description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A method of manufacturing a catheter shaft having a distal tip, the catheter shaft having an inner surface and an outer surface and a distal end and a proximal end, the distal tip having an inner surface and an outer surface and a length, the method comprising the steps of:

providing said catheter shaft and said distal tip, said distal tip having a portion engaged to the catheter shaft along a length of the distal end, the entire length of the portion disposed about and engaged to the outer surface of the catheter shaft having an inner surface and an outer surface that are parallel to one another; and rounding the inner surface of the distal tip by ablating such that the circumference of the inner surface increases in a longitudinal direction toward the distal tip.

2. The method of claim 1 further comprising the step of rounding the outer surface of the distal tip.

3. The method of claim 1 wherein the rounding step comprises laser ablation of material from the surface.

4. The method of claim 3 wherein said laser is an ultraviolet laser.

5. The method of claim 3 wherein said laser produces UV radiation having a wavelength of about 450 nm or less.

6. The method of claim 3 wherein said laser produces UV radiation having a wavelength of about 351 nm or less.

7. The method of claim 1 wherein the distal tip is integral with said catheter shaft.

8. The method of claim 1 wherein the distal tip is formed separately from said catheter shaft and the method further comprises the steps of disposing the distal tip on the catheter shaft.

9. The method of claim 1 wherein the catheter shaft is formed such that the inner surface has a first circumference at the distal tip and a second circumference proximal the distal tip, wherein the first circumference at the distal tip is at least 10% larger than the second circumference proximal the distal tip.

10. The method of claim 1 wherein the distal tip is formed from a polymeric material which is softer than said polymeric material from which said catheter shaft is formed as measured by a Shore Durometer scale.

* * * * *